United States Patent [19]

Kajihara et al.

[11] Patent Number: 5,504,098
[45] Date of Patent: Apr. 2, 1996

[54] BENZOTHIAZOLESULFONAMIDE DERIVATIVE, METHOD FOR PREPARING THE SAME, AND USE THEREOF

[75] Inventors: Akiro Kajihara; Masahiko Tsuchiya, both of Nobeoka, Japan

[73] Assignee: Asahi Kasei Kogyo Kabushiki Kaisha, Osaka, Japan

[21] Appl. No.: 318,682

[22] PCT Filed: Jan. 20, 1994

[86] PCT No.: PCT/JP94/00071

§ 371 Date: Feb. 9, 1995

§ 102(e) Date: Feb. 9, 1995

[87] PCT Pub. No.: WO94/19336

PCT Pub. Date: Sep. 1, 1994

[30] Foreign Application Priority Data

Feb. 19, 1993 [JP] Japan .................... 5-030007

[51] Int. Cl.⁶ .................... A61K 31/425; C07D 277/64; C07D 417/14; C07D 417/12

[52] U.S. Cl. .................... 514/367; 548/178; 544/368; 544/238; 544/333; 514/254; 514/210; 514/218; 514/253; 514/255; 514/256; 540/470; 540/553; 540/575; 549/435

[58] Field of Search .................... 548/178; 514/367, 514/254; 544/368

[56] References Cited

U.S. PATENT DOCUMENTS

3,852,298 12/1974 Wagner et al. .................... 260/304
5,326,870 7/1994 Kajihara et al. .................... 540/575

FOREIGN PATENT DOCUMENTS

9214712 9/1992 WIPO.
9408962 4/1994 WIPO.

OTHER PUBLICATIONS

Morikawa, et al., J. Med. Chem. (1989), 32, 42–46.
Cremlyn et al., Phos. Sulf. Silicon (1992), 73(1–4), 107–120.

Primary Examiner—Johann Richter
Assistant Examiner—Laura R. Cross
Attorney, Agent, or Firm—Finnegan, Henderson, Farabow, Garrett & Dunner

[57] ABSTRACT

Disclosed are a benzothiazolesulfonamide derivative represented by the formula (I) or a pharmaceutically acceptable acid addition salt thereof

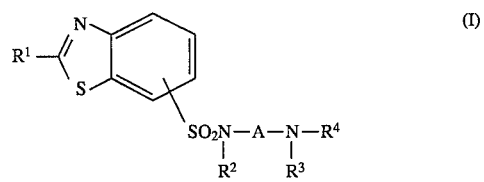

wherein A represents a lower alkylene group which is unsubstituted or substituted; $R^1$ represents a hydrogen atom or a lower alkyl group; each of $R^2$ and $R^3$ independently represents a hydrogen atom or a lower alkyl group, or $R^2$ and $R^3$ are bonded together to form a lower alkylene group which is unsubstituted or substituted; and $R^4$ represents a hydrogen atom, a lower alkyl group, an amidino group, or a phenyl-substituted lower alkyl group, wherein the lower alkyl group is substituted or unsubstituted, and the phenyl group is unsubstituted or substituted with a lower alkyl group, a lower alkoxy group, a halogen atom or a methylenedioxy group;

a method for preparing the same; and a pharmaceutical composition comprising the same. Each of the benzothiazolsulfonamide derivative of the formula (I) of the present invention and the acid addition salt thereof has the activity to inhibit a protein kinase and can therefore be advantageously used as an active ingredient for a reagent for the treatment and prevention of asthma.

3 Claims, No Drawings

BENZOTHIAZOLESULFONAMIDE DERIVATIVE, METHOD FOR PREPARING THE SAME, AND USE THEREOF

This application is a 371 of PCT/JP94/0071 filed Jan. 20, 1994.

TECHNICAL FIELD

The present invention relates to a novel benzothiazolesulfonaimde derivative, a method for preparing the same, and a pharmaceutical use thereof.

BACKGROUND ART

In International Patent Application Publication No. WO92/14712, there is disclosed a benzothiazolesulfonylaminoethyl derivative, more specifically, 1-[2-(6-benzothiazolesulfonylamino)ethyl]-4-[3-(phenoxy)propyl]piperazine, which has the ability to relax a bronchial smooth muscle by its antihistaminic activity. However, there is no description teaching or suggesting that the above-mentioned benzothiazolesulfonylaminoethyl derivative has a protein kinase inhibiting activity.

DISCLOSURE OF THE INVENTION

In a living body, various types of protein kinases, such as protein kinase C, cyclic AMP-dependent kinase, cyclic GMP-dependent kinase and myosin light chain kinase, are present. With respect to the inhibitors for the above protein kinases, there have been proposed and expected various uses, such as a drug for circulatory organ diseases and a carcinostatic agent. Recently, it has been strongly desired to provide a compound having other protein kinase inhibiting activity as compared to the protein kinase inhibiting activities of the known protein kinase inhibitors.

The present inventors have made extensive and intensive studies with a view toward developing a compound which exhibits an excellent protein kinase inhibiting activity. As a result, it has been found that a specific benzothiazolesulfonamide derivative which is represented by the formula (I) described below has an excellent activity to inhibit protein kinase C and myosin light chain kinase. Based on the above finding, the present invention has been completed.

According to one aspect of the present invention, there is provided a benzothiazolesulfonamide derivative represented by the formula (I) or a pharmaceutically acceptable acid addition salt thereof

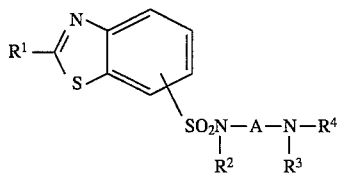

wherein A represents a $C_{2-6}$ alkylene group which is unsubstituted or substituted with a $C_{1-4}$ alkyl group; $R^1$ represents a hydrogen atom or a $C_{1-4}$ alkyl group; each of $R^2$ and $R^3$ independently represents a hydrogen atom or a $C_{1-6}$ alkyl group, or $R^2$ and $R^3$ are bonded to each other to form a $C_{1-4}$ alkylene group which is unsubstituted or substituted with a $C_{1-4}$ alkyl group; and $R^4$ represents a hydrogen atom, a $C_{1-6}$ alkyl group, an amidino group, or a group represented by the formula (II)

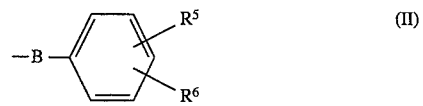

wherein B represents a $C_{1-6}$ alkylene group which is unsubstituted or substituted with a $C_{1-4}$ alkyl group; and each of $R^5$ and $R^6$ independently represents a hydrogen atom, a $C_{1-6}$ alkyl group, a $C_{1-6}$ alkoxy group or a halogen atom, or $R^5$ and $R^6$ are bonded to each other to form a methylenedioxy group.

According to another aspect of the present invention, there is provided a method for preparing a benzothiazolesulfonamide derivative represented by the formula (I) as mentioned above or a pharmaceutically acceptable acid addition salt thereof, which comprises reacting, in an inert solvent, a compound represented by the formula (III)

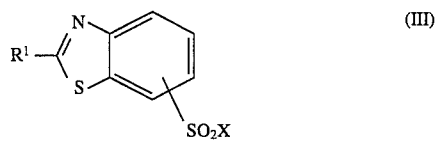

wherein X represents a halogen atom, and $R^1$ has the same meaning as defined for the formula (I) above,
with an amine represented by the formula (IV)

wherein A $R^2$, $R^3$ and $R^4$ have the same meanings as defined for the formula (I) above.

According to a further aspect of the present invention, there is provided a reagent for the treatment and prevention of asthma, having a protein kinase inhibiting activity, which comprises, as an active ingredient, a benzothiazolesulfonamide derivative represented by the formula (I) as mentioned above or a pharmaceutically acceptable acid addition salt thereof.

According to still a further aspect of the present invention, there is provided a pharmaceutical composition comprising a benzothiazolesulfonamide derivative represented by the formula (I) as mentioned above or a pharmaceutically acceptable acid addition salt thereof, and at least one pharmaceutically acceptable carrier or diluent.

In the above formula (I), A represents a $C_{2-6}$ alkylene group which is unsubstituted or substituted with a $C_{1-4}$ alkyl group. Examples of such alkylene groups include an ethylene group, a trimethylene group, a tetramethylene group, a pentamethylene group and a hexamethylene group. Of these, an ethylene group is especially preferred. The above $C_{2-6}$ alkylene group as A can be substituted with a linear or branched $C_{1-4}$ alkyl group, such as a methyl group, an ethyl group, a propyl group, an isopropyl group, a butyl group, an isobutyl group, a 1-methylpropyl group or a t-butyl group.

In the above formula (I), when $R^1$ represents a $C_{1-4}$ alkyl group, $R^1$ has a linear or branched structure. Examples of such $C_{1-4}$ alkyl groups include a methyl group, an ethyl group, a propyl group, an isopropyl group, a butyl group, an isobutyl group, a 1-methylpropyl group and a t-butyl group. Of these, a methyl group and an ethyl group are especially preferred.

In the above formula (I), when each of $R^2$ and $R^3$ independently represents a $C_{1-6}$ alkyl group, it has a linear or branched structure. Examples of such $C_{1-6}$ alkyl groups include a methyl group, an ethyl group, a propyl group, an isopropyl group, a butyl group, an isobutyl group, a 1-methylpropyl group, a t-butyl group, a pentyl group and a hexyl group. Of these, a methyl group, an ethyl group and a propyl group are especially preferred. $R^2$ and $R^3$ can be bonded to each other to form a $C_{1-4}$ alkylene group. Examples of such $C_{1-4}$ alkylene groups include a methylene group, an ethylene group, a trimethylene group and a tetramethylene group. Of these, an ethylene group and a trimethylene group are preferred. The above $C_{1-4}$ alkylene group formed by the bonding between $R^2$ and $R^3$ can be substituted with a linear or branched $C_{1-4}$ alkyl group, such as a methyl group, an ethyl group, a propyl group, an isopropyl group, a butyl group, an isobutyl group, a 1-methylpropyl group or a t-butyl group. Of these, a methylethylene group is preferred.

In the above formula (I), when $R^4$ represents a $C_{1-6}$ alkyl group, $R^4$ has a linear or branched structure. Examples of such $C_{1-6}$ alkyl groups include a methyl group, an ethyl group, a propyl group, an isopropyl group, a butyl group, an isobutyl group, a 1-methylpropyl group, a t-butyl group, a pentyl group and a hexyl group.

Further, when $R_4$ is a group represented by the formula (II), a benzene ring thereof is unsubstituted, or mono-substituted or di-substituted with a $C_{1-6}$ alkyl group, a $C_{1-6}$ alkoxy group or a halogen atom as $R^5$ or $R^6$, or substituted with a methylenedioxy group which is formed by bonding between $R^5$ and $R^6$. $R^5$ and $R^6$ may be the same or different. The above-mentioned $C_{1-6}$ alkyl group has a linear or branched structure. Examples of such $C_{1-6}$ alkyl groups include a methyl group, an ethyl group, a propyl group, an isopropyl group, a butyl group, an isobutyl group, a 1-methylpropyl group, a t-butyl group, a pentyl group and a hexyl group. The above-mentioned $C_{1-6}$ alkoxy group also has a linear or branched structure. Examples of such $C_{1-6}$ alkoxy groups include a methoxy group, an ethoxy group, a propoxy group, an isopropoxy group, a butoxy group, an isobutoxy group, a 1-methylpropoxy group, a t-butoxy group, a pentyloxy group and a hexyloxy group. Examples of halogen atoms as $R^5$ and $R^6$ include a chlorine atom, a bromine atom and a fluorine atom.

In the formula (II), B represents a $C_{1-6}$ alkylene group which is unsubstituted or substituted with a $C_{1-4}$ alkyl group. Examples of such $C_{1-6}$ alkylene groups include a methylene group, an ethylene group, a trimethylene group, a tetramethylene group, a pentamethylene group and a hexamethylene group. Of these, an ethylene group is especially preferred. The above $C_{1-6}$ alkylene group as B is unsubstituted or substituted with a linear or branched $C_{1-4}$ alkyl group, such as a methyl group, an ethyl group, a propyl group, an isopropyl group, a butyl group, an isobutyl group, a 1-methylpropyl group or a t-butyl group.

As the groups represented by the formula (II) as mentioned above, preferred are a benzyl group and a phenylethyl group, each of which is unsubstituted or substituted with a halogen atom or a methylenedioxy group.

With respect to the benzothiazolesulfonaimde derivative of the formula (I) of the present invention, specific examples include:
(1) 1-(7-benzothiazolesulfonyl)homopiperazine,
(2) 1-(7-benzothiazolesulfonyl)piperazine,
(3) 1-(7-benzothiazolesulfonyl)-2-methylpiperazine,
(4) 1-(7-benzothiazolesulfonyl)ethylenediamine,
(5) 1-(7-benzothiazolesulfonyl)-4-methylethylenediamine,
(6) 1-(6-benzothiazolesulfonyl)piperazine,
(7) N-[2-(3,4-methylenedioxybenzylamino)ethyl]-7-benzothiazolesulfonamide,
(8) N-[2-(3-chlorobenzylamino)ethyl]-7-benzothiazolesulfonamide,
(9) N-[2-[1-(3-chlorophenyl)ethyl]aminoethyl]-7-benzothiazolesulfonamide, and
(10) N-[2-(3-fluorobenzylamino)ethyl]-7-benzothiazolesulfonamide.

Further, in the present invention, the benzothiazolesulfonamide derivative of the formula (I) can be in the form of an acid addition salt thereof. This salt is a pharmaceutically acceptable, non-toxic salt. Examples of acid addition salts of the benzothiazolesulfonamide derivative (I) include salts with inorganic acids, such as hydrochloric acid, hydrobromic acid, phosphoric acid and sulfuric acid, and salts with organic acids, such as acetic acid, citric acid, tartaric acid, lactic acid, succinic acid, fumaric acid, maleic acid, methanesulfonic acid, glutamic acid and aspertic acid. Also acid addition salts of the benzothiazolesulfonamide derivative (I) with other known acids can be employed.

The benzothiazolesulfonamide derivative of the present invention can be produced by various methods. For example, there can be employed a method in which a compound represented by the above-mentioned formula (III) is reacted with an amine represented by the above-mentioned formula (IV) in an inert solvent.

The compound of the formula (III) can be obtained by converting a sulfonic acid represented by the formula (V)

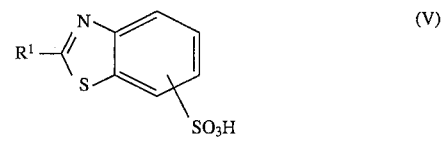

wherein $R^1$ has the same meaning as defined for the formula (I) above,
to a sulfonyl halide by a conventional method. For example, there can be mentioned a method in which the sulfonic acid represented by the formula (V) is chlorinated using thionyl chloride, thereby obtaining a sulfonyl chloride.

As an inert solvent which is used in the reaction between compound (III) and amine (IV) in the method of the present invention, there can be employed halogenated hydrocarbons, such as dichloromethane and chloroform; ethers, such as tetrahydrofuran, dioxane and diethyl ether; dimethylsulfoxide; N,N-dimethylformamide; and acetonitrile. These solvents can be used individually or in combination.

It is preferred that the reaction between compound (III) and amine (IV) be conducted in the presence of an acid acceptor. Examples of acid acceptors include alkali metal compounds, such as sodium hydrogencarbonate, sodium hydroxide, potassium carbonate, sodium carbonate, potassium hydroxide and sodium methylate, and organic tertiary amines, such as pyridine, trimethylamine and triethylamine.

In the method of the present invention, it is preferred that the amount of the amine (IV) be in the range of from 1 to 20 moles, more preferably from 1 to 10 moles, per mole of the compound (III). When the reaction between compound (III) and amine (IV) is conducted in the absence of an acid acceptor, it is preferred that the amount of the amine (IV) be in the range of from 2.5 to 5 moles per mole of the compound (III). When the reaction between compound (III) and amine (IV) is conducted in the presence of an acid acceptor, it is preferred that the amount of the amine (IV) be in the range of from 1 to 3 moles per mole of the compound (III).

The reaction temperature is generally in the range of from −30° C. to 120° C., preferably from −20° C. to 50° C. The reaction time is generally 0.5 to 48 hours, preferably 0.5 to 6 hours. The progress of the reaction can be observed by thin layer chromatography (TLC) or high performance liquid chromatography (HPLC), so that the reaction can be terminated when it is observed that the compound (III) is completely consumed.

The desired benzothiazolesulfonamide derivative represented by formula (I) obtained by the reaction between the compound (III) and amine (IV) is collected from the reaction mixture in the form of a free base. When a hydrophilic solvent is employed as a reaction solvent, the resultant reaction solvent is removed from the reaction mixture by distillation to obtain a residue. The obtained residue is dissolved in a hydrophobic solvent. The resultant solution is washed with an aqueous weakly alkaline solution, water or the like and, then, the hydrophobic solvent is removed from the solution by distillation, thereby obtaining benzothiazolesulfonamide derivative (I). When a hydrophobic solvent is employed as a reaction solvent, the resultant reaction mixture is directly washed with an aqueous weakly alkaline solution, water or the like, followed by removal of the solvent by distillation, thereby obtaining benzothiazolesulfonamide derivative (I).

An acid addition salt of the benzothiazolesulfonamide derivative (I) of the present invention can be produced by conventional methods. For example, the benzothiazolesulfonamide derivative (I) is dissolved in an alcohol, such as methanol or ethanol, to obtain a solution. Then, an equiamount or several-fold amount of an acid is added to the solution to form an acid addition salt. Examples of acids include inorganic acids, such as hydrochloric acid, hydrobromic acid, phosphoric acid and sulfuric acid, and organic acids, such as acetic acid, citric acid, tartaric acid, lactic acid, succinic acid, fumaric acid, maleic acid, methanesulfonic acid, glutamic acid and aspartic acid. Also, other known acids can be used for producing an acid addition salt of the benzothiazolesulfonamide derivative of the present invention. In addition, the benzothiazolesulfonamide derivative of the present invention can be obtained by treating the above-mentioned acid addition salt with an alkali by a known method.

The purification of the benzothiazolesulfonamide derivative (I) or an acid addition salt thereof can be conducted by conventional methods, such as recrystallization and column chromatography using known carriers, e.g., silica gel.

The benzothiazolesulfonamide derivative (I) of the present invention or a pharmaceutically acceptable acid addition salt thereof (hereinafter frequently referred to simply as "compound of the present invention") exhibits a high protein kinase inhibiting activity. Further, even when the compound of the present invention was orally administered to rats in an amount as large as 300 mg per kg of a rat, none of the rats died. That is, the compound of the present invention is safe and therefore can be advantageously used as an active ingredient for a medicine.

Accordingly, as mentioned above, in still a further aspect of the present invention, there is provided a pharmaceutical composition comprising a benzothiazolesulfonamide derivative represented by formula (I) or a pharmaceutically acceptable acid addition salt thereof, and at least one pharmaceutically acceptable carrier or diluent.

The pharmaceutical composition of the present invention can be in various forms, such as a tablet, powder, granule, syrup, suspension, capsule and reagent for injection. Depending on the form of the medicine, a suitable type of a carrier to be used for the compound of the present invention is selected. Examples of carriers to be used for a medicine for oral administration include excipients, such as lactose, refined sugar, glucose, starch and crystalline cellulose; binders, such as hydroxypropyl cellulose, carboxymethyl cellulose, starch, gum arabic, gelatin, glucose, refined sugar, tragacanth and sodium alginate; disintegrators, such as carboxymethyl cellulose, starch and calcium carbonate; lubricants, such as stearic acid, refined talc, sucrose fatty acid ester, hydrated vegetable oil, magnesium stearate and calcium stearate; surfactants, such as sodium lauryl sulfate, soybean lecithine, sucrose fatty acid ester and polysorbate 80; additives such as lecithine, soybean oil and glycerin; a flowability agent; and a coloring agent. When the compound of the present invention is formulated into an inhalant, polychloromonofluoromethane or the like may be used as a solvent.

When the compound of the present invention is formulated into a medicine for parenteral administration (e.g., a reagent for injection), distilled water for injection, physiological saline, an aqueous solution of glucose, a vegetable oil for injection, propylene glycol and polyethylene glycol and the like can be used as a diluent. If desired, other additives, such as a germicide, an antiseptics, a stabilizer, an isotonizing agent and a soothing agent, can be used in combination with the diluent.

When the compound of the present invention is administered to human, the compound may be orally administered in the form of a tablet, powder, granule, suspension or capsule, or parenterally administered in the form of a reagent for injection including intravenous administration, a cream or a spray. The dose is varied depending on the age, weight, condition, etc. of the patient. However, the dose may generally be in the range of from 3 to 300 mg per day for an adult. The daily dose may be administered at one time, or it may also be divided into 2 or 3 portions and these portions are administered at intervals. The administration is generally continued for a period of from several days to 2 months. The daily dose and the administration period are varied to some extent, depending on the condition of the patient.

Best Mode for Carrying Out the Invention

Hereinbelow, the present invention will be described in more detail with reference to the following Examples but they should not be construed to be limiting the scope of the present invention.

With respect to each of compounds 1 to 10, respectively, obtained in Examples 1 to 10, NMR spectrum and mass spectrum are shown in Table 3 below.

Example 1

1-(7-benzothiazolesulfonyl)homopiperazine hydrochloride (compound 1)

To 12 g of 7-benzothiazolesulfonic acid were added 120 ml of thionyl chloride and 1.2 ml of dimethylformamide. The resultant mixture was heated under reflux for 3 hours and the thionyl chloride was removed by distillation under reduced pressure to obtain a residue. The thus obtained residue was dissolved in 100 ml of ice water and adjusted to a pH of 6 with a saturated aqueous sodium carbonate solution. The resultant solution is subjected to extraction with 100 ml of dichloromethane, followed by separation of a dichloromethane phase. The dichloromethane phase was dropwise added to 100 ml of a dichloromethane solution containing 16.8 g of homopiperazine over 30 minutes while cooling with ice. The resultant mixture was stirred at a temperature of 0° C. to 5° C. for 1 hour to carry out a reaction. After completion of the reaction, the resultant mixture was washed with 200 ml of water and dried over anhydrous magnesium sulfate. Then, solvent removal was conducted by distillation under reduced pressure to obtain a residue. The thus obtained residue was subjected to purification by means of a chromatography column packed with 600 g of silica gel (Wakogel C-200, manufactured and sold by Wako Pure Chemical Industries, Ltd., Japan), using a mixed solvent of methanol and chloroform (5 to 10% methanol) as an eluent, to thereby obtain 10.8 g of 1-(7-benzothiazolesulfonyl)homopiperazine (yield: 65%).

2.8 g of the obtained 1-(7-benzothiazolesulfonyl)homopiperazine was dissolved in 20 ml of methanol. To the resultant solution was added an equal amount of aqueous hydrochloric acid. The resultant mixture was stirred for 10 minutes. Then, solvent removal was conducted by distillation under reduced pressure to obtain a residue. The thus obtained residue was subjected to recrystallization, using a mixed solvent of ethanol and water, to thereby obtain 2.7 g of 1-(7-benzothiazolesulfonyl)homopiperazine hydrochloride (compound 1) (yield: 86%).

Example 2

1-(7-benzothiazolesulfonyl)piperazine hydrochloride (compound 2)

Substantially the same procedure as in Example 1 was repeated, except that 14.4 g of piperazine was used instead of 16.8 g of homopiperazine, to thereby obtain compound 2.

Example 3

1-(7-benzothiazolesulfonyl)-2-methylpiperazine hydrochloride (compound 3)

Substantially the same procedure as in Example 1 was repeated, except that 16.8 g of 2-methylpiperazine was used instead of 16.8 g of homopiperazine, to thereby obtain compound 3.

Example 4

1-(7-benzothiazolesulfonyl)ethylenediamine hydrochloride (compound 4)

To 12 g of 7-benzothiazolesulfonic acid were added 120 ml of thionyl chloride and 1.2 ml of dimethylformamide. The resultant mixture was heated under reflux for 3 hours, and the thionyl chloride was removed by distillation under reduced pressure to obtain a residue. The thus obtained residue was dissolved in 100 ml of ice water and adjusted to a pH of 6 with a saturated aqueous sodium carbonate solution. The resultant solution was subjected to extraction with 100 ml of dichloromethane, followed by separation of a dichloromethane phase. The dichloromethane phase was dropwise added to 100 ml of a dichloromethane solution containing 10.1 g of ethylenediamine over 30 minutes while cooling with ice. The resultant mixture was stirred at a temperature of 0° C. to 5° C. for 1 hour to carry out a reaction. After completion of the reaction, 200 ml of water was added to the resultant mixture and adjusted to a pH of 4 to 6. Then, the aqueous phase was separated from the mixture, and the separated aqueous phase was dried under reduced pressure, thereby obtaining a residue. The thus obtained residue was subjected to recrystallization using water, to thereby obtain 8.8 g of 1-(7-benzothiazolesulfonyl)ethylenediamine hydrochloride (compound 4) (yield: 54%).

Example 5

1-(7-benzothiazolesulfonyl)-4-methylethylenediamine hydrochloride (compound 5)

Substantially the same procedure as in Example 4 was repeated, except that 12.4 g of 1-methylethylenediamine was used instead of 10.1 g of ethylenediamine, to thereby obtain compound 5.

Example 6

1-(6-benzothiazolesulfonyl)piperazine hydrochloride (compound 6)

Substantially the same procedure as in Example 1 was repeated, except that 12 g of 6-benzothiazolesulfonic acid was used instead of 12 g of 7-benzothiazolesulfonic acid, and 14.4 g of piperazine was used instead of 16.8 g of homopiperazine, to thereby obtain compound 6.

Examples 7 to 10

N-[2-(3,4-methylenedioxybenzylamino)ethyl]-7-benzothiazolesulfonamide hydrochloride (compound 7),
N-[2-(3-chlorobenzylamino)ethyl]-7-benzothiazolesulfonamide hydrochloride (compound 8),
N-{2-[1-(3-chlorophenyl)ethyl]aminoethyl}-7-benzothiazolesulfonamide hydrochloride (compound 9), and
N-[2-(3-fluorobenzylamino)ethyl]-7-benzothiazolesulfonamide hydrochloride (compound 10)

Substantially the same procedure as in Example 1 was repeated in each of Examples 7 to 10, except that, instead of 16.8 g of homopiperazine, 32.6 g of 1-(3,4-methylenedioxybenzyl)-ethylenediamine, 31.0 g of 1-(3-chlorobenzyl)-ethylenediamine, 33.3 g of 1-[1-(3-chlorophenyl)ethyl]-ethylenediamine, and 28.2 g of 1-(3-fluorobenzyl)-ethylenediamine were, respectively, used in Examples 7 to 10, to thereby obtain compounds 7 to 10, respectively.

Example 11

Measurement of the activity to inhibit Myosin light chain kinase (MLCK)

Each of compounds 1 to 10 was used as an inhibitor for MLCK. As a comparative compound, 1-[2-(6-benzothiazolesulfonylamino)ethyl]-4-[3-(phenoxy)propyl] piperazine dihydrochloride disclosed in International Patent Application Publication No. WO92/14712 was used.
(1) Measurement of an MLCK inhibiting activity
Measurement of an MLCK inhibiting activity of each of compounds 1 to 10 was conducted utilizing the reaction system of MLCK and an antibody specific for phosphorylated myosine light chain (MLCP). MLC was isolated from a chicken gizzard and purified by the method according to Perry et al. (Journal of Biochemistry, vol. 211, p.267–272, 1983), to thereby obtain 20 kDa of purified MLC. On the other hand, MLCK was isolated and purified by the method according to Walsh et al. (Methods in Enzymology, vol. 99, p.279–288, 1983). Calmodulin was isolated from a pig brain and purified by the method according to Yazawa (Journal of Biochemistry, vol. 87, p.1313–1320, 1980). Further, anti-MLCP antibody was prepared by using, as an antigen, a synthetic peptide which has an amino acid sequence of an MLCP amino acid fragment of 12 amino acid residues containing a serine residue (phosphorylation site of MLCP). Illustratively stated, a peptide having a 12 amino acid sequence of the 11th lysine residue through the 22nd phenylalanine (counted from the N-terminus amino acid of MLCP) and a cysteine residue attached to the C-terminus of the 12 amino acid sequence, was synthesized (KKRPQRATSNVFC). The synthetic peptide was subjected to phosphorylation by MLCK in the presence of ATP, followed by purification by high performance liquid chromatography. The purified peptide was conjugated with key hole limpet hemocyanin (KLH). The conjugation efficiency thereof was 110–148 nmol peptide/mg KLH. 0.2 mg of the KLH-conjugated peptide was mixed with an adjuvant and injected to a rabbit. The injection was conducted four more times, to thereby immunize the rat. An anti-MLCP antibody was obtained from the rat, and the antibody titer thereof was examined. With respect to the anti-MLCP antibody having a satisfactorily high antibody titer, an IgG fraction (anti-MLCP IgG) was obtained and purified.

Measurement of the MLCK activity was conducted as follows.

MLC was diluted with a phosphate buffer (PBS) to obtain a solution having a MLC concentration of 5 µg/ml. 100 µl of the solution was added to each well of 96-well immunoplate, and was allowed to stand overnight at 4° C., to thereby immobilize the MLC on the surface of each well. Each plate was washed with PBS to thereby remove the MLC which had not been immobilized. To each of the MLC-immobilized wells was added a solution containing 25 mM Tris buffer (pH 7.5), 3 mM magnesium chloride, 1 mM calcium chloride, 0.1% of 2-mercaptoethanol, 1 mg/ml bovine serum albumin, 20 µg/ml calmoduline, 0.1 µg/ml MLCK, and 20 µM of ATP, thereby initiating the reaction. Substantially the same reaction as mentioned above was repeated three more times, except that the ATP concentration was changed to 30, 50 and 100 µM. 3 Minutes after the initiation of each of the reactions, 100 µl of an aqueous 20% phosphoric acid solution was added to each well of the individual plates to terminate the reaction. Each well was washed three times with PBS containing 0.2% of Triton X-100 (TrPBS). As a primary antibody, 100 µl of anti-MLCP antibody which had been diluted 500-fold with PBS containing 0.05% Tween 20 (TwPBS) was added to each of the washed wells, and allowed to stand at room temperature for 1 hour. Each well was washed with TrPBS three times. Then, as a secondary antibody, 100 µl of peroxydase-labeled anti-rabit IgG antibody (manufactured and sold by Cappel Co., Ltd., Germany) which had been diluted 1000-fold with TwPBS was added to each well, and allowed to stand at room temperature for 1 hour. Each well was washed with TrPBS three times. To each well was added 100 µl of a coloring agent containing 2 mg/ml orthophenylenediamine and an aqueous 0.04% hydrogen peroxide solution. When the coloring proceeded satisfactorily, 30 µl of 4.5M sulfuric acid was added to each well to terminate the reaction. The absorbance of the reaction mixture in each well was determined using a microplate reader (manufactured and sold by Bio-Rad laboratories, U.S.A.). The absorbance values of the respective resultant reaction mixtures having ATP concentrations of 20, 30, 50 and 100 µM show that the absorbance is in proportion to the amount of phosphorylated MLC. Thus, it was confirmed that the absorbance can be taken as an MLCK activity.

In order to measure the MLCK inhibiting activity of each of compounds 1 to 10 and the comparative compound, each of the compounds having an appropriate concentration was individually added to the abovementioned respective solutions having ATP concentrations of 20, 30, 50 and 100 µM and, then, the MLCK activity was individually measured in terms of the absorbance in substantially the same manner as mentioned above. The MLCK inhibiting activity in terms of inhibition constant (Ki) was individually obtained by double reciprocal plotting of the respective MLCK activities obtained in the presence of each of compounds 1 to 10 and the comparative compound, and the respective MLCK activities obtained in the absence of compounds 1 to 10 and the comparative compound.

(2) Results of the measurements
Results are shown in Table 1.

Example 12

Measurement of the activity to inhibit protein kinase C (PKC)

Each of compounds 1 to 10 was used as an inhibitor for PKC. As a comparative compound, 1-[2-(6-benzothiazole-sulfonylamino)ethyl]-4-[3-(phenoxy)propyl]piperazine dihydrochloride disclosed in International Patent Application Publication No. WO92/14712 was used.

(1) Measurement of a PKC inhibiting activity

Measurement of a PKC inhibiting activity of each of compounds 1 to 10 was conducted utilizing a kit for measuring PKC inhibiting activity (manufactured and sold by Medical and Biological Laboratories, Japan). PKC was isolated from a rat brain and purified by the method according to Inagaki et al. (Journal of Biochemistry, vol. 260, p.2922–2925, 1985). On the surface of each well of the 96-well plate of the measuring kit, a peptide which is a substrate for PKC was immobilized. To each of the wells was added a solution containing 25 mM Tris buffer (pH 7.5), 3 mM magnesium chloride, 1 mM calcium chloride, 0.1% 2-mercaptoethanol, 1 mg/ml bovine serum albumin, 50 µg/ml phosphatidylserine, 10 µg/ml PKC and 1 µM of ATP, thereby initiating the reaction. Substantially the same reaction as mentioned above was repeated three more times, except that the ATP concentration was changed to 3, 5 and 10 µM. 3 Minutes after the initiation of each of the reactions, 100 µl of an aqueous 20% phosphoric acid solution was added to each well of the individual plates to terminate the reaction. Each well was washed with TrPBS three times. 100 µl of the primary antibody included in the kit, which had been diluted 10-fold with TwPBS, was added to each of the washed wells, and allowed to stand at room temperature for 1 hour. Each well was washed with TrPBS three times. Then, as a secondary antibody, 100 µl of peroxydase-labeled anti-mouse IgG antibody (manufactured and sold by Bio-Rad laboratories, U.S.A.) which had been diluted 1000-fold with TwPBS was added to each well, and allowed to stand at room temperature for 1 hour. Each well was washed with TrPBS three times. To each well was added 100 µl of a coloring agent containing 2 mg/ml orthophenylenediamine and an aqueous 0.04% hydrogen peroxide solution. When the coloring proceeded satisfactorily, 30 µl of 4.5M sulfuric acid was added to each well to terminate the reaction. The absorbance of the reaction mixture in each well was determined using a microplate reader (manufactured and sold by Bio-Rad laboratories, u.s.a.).

In order to measure the PKC inhibiting activity of each of compounds 1 to 10 and the comparative compound, each of the compounds having an appropriate concentration was individually added to the above-mentioned respective solutions having ATP concentrations of 1, 3, 5 and 10 µM and, then, the PKC activity was individually measured in terms of the absorbance in substantially the same manner as mentioned above. The PKC inhibiting activity in terms of inhibition constant (Ki) was individually obtained by double reciprocal plotting of the respective PKC activities obtained in the presence of each of compounds 1 to 10 and the comparative compound, and the respective PKC activities obtained in the absence of compounds 1 to 10 and the comparative compound.

(2) Results of the measurements
Results are shown in Table 1.

TABLE 1

| Inhibitor | PKC inhibiting activity in terms of Ki value (µM) | MLCK inhibiting activity in terms of Ki value (µM) |
| --- | --- | --- |
| Compound 1 | 7 | 80 |
| Compound 2 | 5 | 50 |
| Compound 3 | 15 | 90 |
| Compound 4 | 5 | 75 |
| Compound 5 | 35 | 120 |
| Compound 6 | 15 | 25 |

TABLE 1-continued

| Inhibitor | PKC inhibiting activity in terms of Ki value (μM) | MLCK inhibiting activity in terms of Ki value (μM) |
|---|---|---|
| Compound 7 | 6 | 50 |
| Compound 8 | 5 | 55 |
| Compound 9 | 25 | 90 |
| Compound 10 | 7 | 55 |
| Comparative compound | >200 | >200 |

As is apparent from Table 1, each of the compounds of the present invention has the high activity to inhibit myosin light chain kinase (MLCK) and protein kinase C (PKC). However, 1-[2-(6-benzothiazolesulfonylamino)ethyl]-4-[3-(phenoxy)propyl]pyperazine dihydrochloride disclosed in International Patent Application Publication No. WO 92/14712 (comparative compound) has no activity to inhibit the protein kinases.

Example 13

Inhibitory effect on KCl-induced contraction of tracheal specimens excised from guinea pigs
(1) Evaluation of inhibitory effect on KCl-induced contraction According to a method in which tracheal specimens excised from guinea pigs were used (Takagi and Ozawa, "Yakubutsugaku Jikken (Experiments in Pharmacology)", p.100–102, 1960, published by Nanzando, Japan; and Fujiwara and Shibata, "Yakurigaku Kiso Jikenho (Methods of Fundamental Experiments in Pharmacology)" p.131–134, 1982, published by Kyourin, Japan), the relaxing effect of benzothiazolesulfonamide derivatives of the present invention (compounds 1 to 10) on bronchial smooth muscle was evaluated.

From male guinea pigs weighing 350 to 500 g (Hartley strain, Kuroda Junkei Dobutsu), tracheas were excised and each of the excised tracheal specimens was hung in a 20 ml Magnus tube filled with Krebs-Henseleit solution containing 3 μM indomethacin under isometric conditions (initial load: 1.5 g). The solution temperature was kept at 37 °C. in an atmosphere containing 95% $O_2$ and 5% $CO_2$. An aqueous KCl solution was dropwise added into the Magnus tube (final KCl concentration: 20 mM) to contract the tracheal specimen.

On the other hand, each of the compounds of the present invention was dissolved in distilled water or physiological saline and, after the KCl-induced contraction became stable, the compound solution was cumulatively added into the Magnus tube. The relaxing effect of each of the compounds of the present invention on contracted tracheal specimens was evaluated and a dose-response curve was obtained. After the evaluation of the relaxing effect, 100 μM of papaverine was individually added into the Magnus tubes, to thereby obtain a maximum relaxation value. Taking the obtained maximum relaxation value as 100%, the relaxation ratio was calculated with respect to each of thee compounds of the present invention. The number of specimens tested for each compound was 3.

As a comparative compound, 1-[2-(6-benzothiazolesulfonylamino)ethyl]-4-[3-(phenoxy)propyl]piperazine dichloride disclosed in International Patent Application Publication No. WO92/14712 was used. (2) Results of the calculations Results of the calculations are shown in Table 2.

TABLE 2

| Compound | Bronchial smooth muscle-relaxation ratio (%) | Compound | Bronchial smooth muscle-relaxation ratio (%) |
|---|---|---|---|
| Compound 1 | 30.5 | Compound 6 | 27.2 |
| Compound 2 | 24.0 | Compound 7 | 96.8 |
| Compound 3 | 21.1 | Compound 8 | 85.7 |
| Compound 4 | 33.0 | Compound 9 | 74.6 |
| Compound 5 | 22.0 | Compound 10 | 78.0 |
| Comparative compound | 6.8 | | |

As is apparent from Table 2, each of the compounds of the present invention has the high ability to relax a bronchial smooth muscle of a tracheal specimen from a guinea pig, which is in KCl-induced contractions. However, 1-[2-(6-benzothiazolesulfonylamino)ethyl]-4-[3-(phenoxy)propyl] pyperazine dihydrochloride disclosed in International Patent Application No. WO 92/14712 (comparative compound) has no ability to relax such a bronchial smooth muscle.

TABLE 3

| Compound No. | NMR (δppm) (DMSOd$_6$/D$_2$O, TMS) | MS (M/E) |
|---|---|---|
| 1 | 1.9–2.1 (2H), 3.0–3.8 (8H), 7.7–7.9 (1H), 7.9–8.1 (1H), 8.3–8.5 (1H), 9.5–9.6 (1H) | 297 |
| 2 | 3.0–4.1 (8H), 7.7–7.9 (1H), 7.9–8.1 (1H), 8.3–8.5 (1H), 9.5–9.6 (1H) | 283 |
| 3 | 2.5–3.8 (10H), 7.7–7.9 (1H), 7.9–8.1 (1H), 8.3–8.5 (1H), 9.5–9.6 (1H) | 297 |
| 4 | 2.5–3.5 (4H), 7.7–7.9 (1H), 7.9–8.1 (1H), 8.3–8.5 (1H), 9.5–9.6 (1H) | 257 |
| 5 | 2.4–3.7 (7H), 7.7–7.9 (1H), 7.9–8.1 (1H), 8.3–8.5 (1H), 9.5–9.6 (1H) | 271 |
| 6 | 3.0–3.5 (8H), 7.8–8.0 (1H), 8.2–8.4 (1H), 8.6–8.8 (1H), 9.6–9.7 (1H) | 283 |
| 7 | 2.8–3.3 (4H), 4.0–4.1 (2H), 6.0–6.1 (2H), 6.8–7.2 (3H), 7.7–7.9 (1H), 8.0–8.2 (1H), 8.3–8.5 (1H), 9.6–9.7 (1H) | 391 |
| 8 | 2.8–3.3 (4H), 4.2–4.4 (2H), 7.4–7.6 (4H), 7.7–7.9 (1H), 8.0–8.2 (1H), 8.3–8.5 (1H), 9.6–9.7 (1H) | 381 |
| 9 | 1.4–1.7 (3H), 2.5–3.3 (4H), 4.3–4.5 (1H), 7.4–7.6 (4H), 7.7–7.9 (1H), 8.0–8.2 (1H), 8.3–8.5 (1H), 9.6–9.7 (1H) | 395 |
| 10 | 2.8–3.3 (4H), 4.1–4.3 (2H), 7.1–7.6 (4H), 7.7–7.9 (1H), 8.0–8.2 (1H), 8.3–8.5 (1H), 9.6–9.7 (1H) | 365 |

Industrial Applicability

The benzothiazolesulfonamide derivative of the formula (I) of the present invention or a pharmaceutically acceptable acid addition salt thereof has the activity to inhibit protein kinases, such as protein kinase C and myosin light chain kinase, so that it can effectively relax a bronchial smooth muscle of a tracheal specimen from a guinea pig, which is in KCl induced contraction. Therefore, the benzothiazolesulfonamide derivative of the formula (I) of the present invention or a pharmaceutically acceptable acid addition salt thereof can be advantageously used as an active ingredient for a reagent for the treatment and prevention of asthma.

We claim:

1. A benzothiazolesulfonamide derivative represented by the formula (I) or a pharmaceutically acceptable acid addition salt thereof

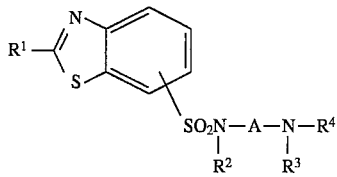
(I)

wherein A represents a $C_{2-6}$ alkylene group which is unsubstituted or substituted with a $C_{1-4}$ alkyl group; $R^1$ represents a hydrogen atom or a $C_{1-4}$ alkyl group; each of $R^2$ and $R^3$ independently represents a hydrogen atom or a $C_{1-6}$ alkyl group, or $R^2$ and $R^3$ are bonded to each other to form a $C_{1-4}$ alkylene group which is unsubstituted or substituted with a $C_{1-4}$ alkyl group; and $R^4$ represents a hydrogen atom, a $C_{1-6}$ alkyl group, an amidino group, or a group represented by the formula (II)

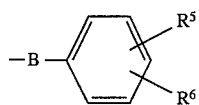
(II)

wherein B represents a $C_{1-6}$ alkylene group which is unsubstituted or substituted with a $C_{1-4}$ alkyl group; and each of $R^5$ and $R^6$ independently represents a hydrogen atom, a $C_{1-6}$ alkyl group, a $C_{1-6}$ alkoxy group or a halogen atom, or $R^5$ and $R^6$ are bonded to each other to form a methylenedioxy group.

2. A pharmaceutical composition comprising: a benzothiazolesulfonamide derivative represented by the formula (I) or a pharmaceutically acceptable acid addition salt thereof

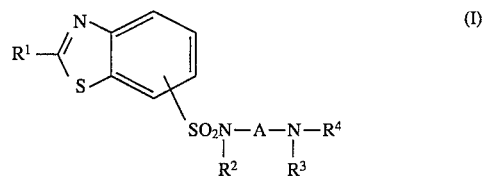
(I)

wherein A represents a $C_{2-6}$ alkylene group which is unsubstituted or substituted with a $C_{1-4}$ alkyl group; $R^1$ represents a hydrogen atom or a $C_{1-4}$ alkyl group; each of $R^2$ and $R^3$ independently represents a hydrogen atom or a $C_{1-6}$ alkyl group, or $R^2$ and $R^3$ are bonded to each other to form a $C_{1-4}$ alkylene group which is unsubstituted or substituted with a $C_{1-4}$ alkyl group; and $R^4$ represents a hydrogen atom, a $C_{1-6}$ alkyl group, an amidino group, or a group represented by the formula (II)

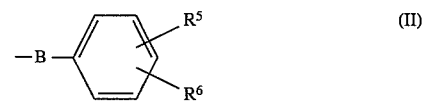
(II)

wherein B represents a $C_{1-6}$ alkylene group which is unsubstituted or substituted with a $C_{1-4}$ alkyl group; and each of $R^5$ and $R^6$ independently represents a hydrogen atom, a $C_{1-6}$ alkyl group, a $C_{1-6}$ alkoxy group or a halogen atom, or $R^5$ and $R^6$ are bonded to each other to form a methylenedioxy group, and at least one pharmaceutically acceptable carrier or diluent.

3. A pharmaceutical composition according to claim 2, which is a reagent for the prevention and treatment of asthma.

* * * * *